(12) United States Patent
Ravi

(10) Patent No.: US 8,192,485 B2
(45) Date of Patent: Jun. 5, 2012

(54) REVERSIBLE HYDROGEL SYSTEMS AND METHODS THEREFOR

(75) Inventor: Nathan Ravi, Chesterfield, MO (US)

(73) Assignees: The United States of America, as represented by the Department of Veterens Affairs, Washington, DC (US); The Washington University in St. Louis, St. Louis, MO (US)

( * ) Notice: Subject to any disclaimer, the term of this patent is extended or adjusted under 35 U.S.C. 154(b) by 2020 days.

(21) Appl. No.: 10/706,081

(22) Filed: Nov. 13, 2003

(65) Prior Publication Data

US 2004/0156880 A1    Aug. 12, 2004

Related U.S. Application Data

(60) Provisional application No. 60/425,764, filed on Nov. 13, 2002.

(51) Int. Cl.
  *A61F 2/16*    (2006.01)
  *A61F 2/14*    (2006.01)

(52) U.S. Cl. ....... 623/6.11; 424/422; 424/427; 424/484; 424/486; 424/78.35; 623/4.1; 977/773

(58) Field of Classification Search .................. 424/422, 424/427; 623/6.11
  See application file for complete search history.

(56) References Cited

U.S. PATENT DOCUMENTS

| | | | | |
|---|---|---|---|---|
| 4,537,943 A * | 8/1985 | Talcott | ............................. | 528/15 |
| 4,892,543 A | 1/1990 | Turley | ................................ | 623/6 |
| 4,932,966 A | 6/1990 | Christie et al. | ..................... | 623/6 |
| 4,994,082 A | 2/1991 | Richards et al. | ................... | 623/6 |
| 5,089,024 A | 2/1992 | Christie et al. | ..................... | 623/6 |
| 5,147,393 A | 9/1992 | Van Noy et al. | .................. | 623/6 |
| 5,158,572 A | 10/1992 | Nielsen | .............................. | 623/6 |
| 5,171,266 A | 12/1992 | Wiley et al. | ........................ | 623/6 |
| 5,173,723 A | 12/1992 | Volk | .............................. | 351/161 |
| 5,192,318 A | 3/1993 | Schneider et al. | ................ | 623/6 |
| 5,217,489 A | 6/1993 | Van Noy et al. | .................. | 623/6 |
| 5,275,623 A | 1/1994 | Sarfarazi | ................................. | 3/6 |
| 5,366,500 A | 11/1994 | Schneider et al. | ................ | 623/6 |
| 5,391,590 A | 2/1995 | Gerace et al. | ................. | 523/107 |
| 5,476,514 A | 12/1995 | Cumming | ......................... | 623/6 |
| 5,476,515 A * | 12/1995 | Kelman et al. | .............. | 623/6.59 |
| 5,489,302 A | 2/1996 | Skottun | .............................. | 623/6 |
| 5,496,366 A | 3/1996 | Cumming | ......................... | 623/6 |
| 5,607,472 A | 3/1997 | Thompson | ........................ | 623/6 |
| 5,674,282 A | 10/1997 | Cumming | ......................... | 623/6 |
| 6,013,101 A | 1/2000 | Israel | ................................. | 623/6 |
| 6,066,172 A | 5/2000 | Huo et al. | ..................... | 623/6.56 |
| 6,117,171 A | 9/2000 | Skottun | ......................... | 623/6.37 |
| 6,176,878 B1 | 1/2001 | Gwon et al. | ................. | 623/6.37 |
| 6,197,059 B1 | 3/2001 | Cumming | .................... | 623/6.39 |
| 6,200,342 B1 | 3/2001 | Tassignon | .................... | 623/6.37 |
| 6,217,612 B1 | 4/2001 | Woods | .......................... | 623/6.37 |
| 6,231,603 B1 | 5/2001 | Lang et al. | ................... | 623/6.37 |
| 6,242,480 B1 * | 6/2001 | Yanni et al. | .................... | 514/458 |
| 6,299,641 B1 | 10/2001 | Woods | .......................... | 623/6.37 |
| 6,387,126 B1 | 5/2002 | Cumming | .................... | 623/6.37 |
| 6,390,622 B1 | 5/2002 | Muckenhirn et al. | ......... | 351/161 |
| 6,443,985 B1 | 9/2002 | Woods | .......................... | 623/6.46 |
| 6,464,725 B2 | 10/2002 | Skotton | ........................ | 623/6.34 |
| 6,494,911 B2 | 12/2002 | Cumming | .................... | 623/6.37 |
| 6,503,276 B2 | 1/2003 | Lang et al. | ..................... | 623/6.37 |
| 6,624,245 B2 | 9/2003 | Wallace et al. | .............. | 525/54.1 |
| 6,730,123 B1 * | 5/2004 | Klopotek | ..................... | 623/6.22 |
| 6,818,018 B1 * | 11/2004 | Sawhney | .................. | 623/11.11 |
| 6,861,065 B2 * | 3/2005 | Hodd et al. | ..................... | 424/427 |
| 2002/0068087 A1 * | 6/2002 | Marchant | ...................... | 424/486 |
| 2003/0143274 A1 * | 7/2003 | Viegas et al. | ................. | 424/486 |

* cited by examiner

*Primary Examiner* — Lezah Roberts
(74) *Attorney, Agent, or Firm* — Gorman Law Offices; Robert S. M. Gorman

(57) ABSTRACT

The present invention relates to reversible hydrogel systems for medical applications. Particularly, the hydrogel of the present invention is made up of copolymers that can be a hydrogel when in an oxidized state and can be a solution when in a reduced state. A solution of the copolymer can be oxidized to form a hydrogel; and the hydrogel can be reduced to form a solution of the copolymer. The solution can be dehydrated to produce the dry copolymer for storage. Furthermore, the present invention also relates to methods of making and using the reversible hydrogel systems.

15 Claims, 8 Drawing Sheets a)

AB-SH + HO$^-$ ⇌ AB-S$^-$ + H$_2$O

AB-S$^-$ + O$_2$ ⟶ AB-S$^\bullet$ + O$_2^-$

2 AB-S$^\bullet$ ⟶ AB-SS-AB b)

AB-SH + RSSR ⇌ AB-SSR + RSH

AB-SH + AB-SSR ⇌ AB-SS-AB + RSH

REVERSIBLE HYDROGEL SYSTEMS AND METHODS THEREFOR

The present invention claims priority to U.S. Provisional Patent Application Ser. No. 60/425,764, filed Nov. 13, 2002.

FIELD OF THE INVENTION

The present invention relates to reversible hydrogel systems. Particularly, the hydrogel of the present invention is made up of copolymers that can be a hydrogel when in an oxidized state and can be a solution when in a reduced state. A solution of the copolymer can be oxidized to form a hydrogel; and the hydrogel can be reduced to form a solution of the copolymer. The solution can be dehydrated to produce the dry copolymer for storage. Furthermore, the present invention also relates to methods of making and using the reversible hydrogel systems.

BACKGROUND OF THE INVENTION

A cataract is a cloudy or opaque area in the normally transparent crystalline lens of the eye. As the opacity increases, it prevents light rays from passing through the lens and focusing on the retina, the light sensitive tissue lining the back of the eye. Early lens changes or opacities may not disturb vision, but as the lens continues to change, several specific symptoms may develop including blurred vision, sensitivity to light and glare, increased nearsightedness, and/or distorted images in either eye.

There are no medications, eye drops, exercises, or glasses that will cause cataracts to disappear once they have formed. When a person is unable to see well enough to perform normal everyday activities, surgery is required to remove the cataract and restore normal vision.

In modern cataract extraction surgery, the cataract is removed from the lens through an opening in the lens capsule. Using an operating microscope, a small incision is made into the eye, and subsequently, the lens capsule. Microsurgical instruments are used to first fragment and then suction the cloudy lens from the eye. The back membrane of the lens (called the posterior capsule) is left in place. The focusing power of the optical system is then restored, usually only for distant vision, by replacement with a permanent pre-fabricated clear plastic intraocular lens (IOL) implant which became popular in the early 1980s.

Prior to the development of IOLs, cataract patients were forced to wear thick "coke bottle" glasses or contact lenses after surgery. Unfortunately, vision is not very good with thick eyeglasses and thick contact lenses do not provide a much better option. The discovery of IOLs solved this problem.

Intraocular lenses can be divided into two main groups: non-foldable and foldable. The original intraocular lenses were made from a hard plastic (non-foldable) material and could therefore be introduced into the eye only with an incision as large as the diameter of the lens. In order to reduce the trauma to the eye in cataract surgery, it is desirable to keep the incision through which the surgical procedure is conducted as small as possible. Foldable lenses are made of acrylic or silicone and can be rolled up and placed inside a tiny tube. The tube is inserted through a very small incision, less than 2.5 mm in length. Once inside the eye, the IOL gently unfolds.

Before the cataract surgery is performed, the corneal curvature and the axial length of the eye of the patient is measured to determine the proper focal power for the IOL that will be inserted. Using sophisticated formulas to calculate the corrective prescription power of the lens, the IOL not only replaces the need for thick glasses, but it can also correct the existing refractive error of the eye.

Although standard IOLs are available in a variety of focal lengths, those lengths are fixed for any given lens. Thus, unlike the natural lens of the eye, a standard IOL is unable to change focus. Therefore, the patient who must rely upon a standard IOL loses accommodative capability after surgery. IOLs are usually chosen that provide adequate distance vision. However, if distance vision is clear, then near vision may be blurred and the patient may require the use of reading glasses following cataract surgery.

Bifocal and multifocal IOLs have been developed to correct this problem. Although they are able to reduce or even eliminate the need for reading glasses, these IOLs produce a reduction in contrast sensitivity and the subjective experience of halos around lights.

A need exists, therefore, for a material that could mimic the natural lens of the eye and thus eliminate the need for reading glasses after cataract surgery. Such a material must be able to change its shape within the eye and thereby its refractive power. In addition to being used as an IOL in cataract surgery, such a material could also be used to treat other refractive errors including presbyopia (the physiologic loss of accommodation in the eyes due to advancing age).

Injectable, in situ forming gels have several potential uses in medicine, e.g., in intra-ocular lenses, as vitreous substitutes, and as drug delivery devices. In general, in situ forming gels have the advantage of being minimally invasive, easily deliverable, and able to fill native or potential cavities while conforming to different shapes, which may otherwise be difficult to prefabricate. The mechanism of gelation may be physical (changes in temperature, hydrogen bonding, hydrophobic interactions) or chemical (ionic or covalent bond formation). Usually, physical crosslinks are less stable than chemical ones. In situ gelation, resulting in networks covalently crosslinked through free-radical polymerization, may be initiated by heat, chemical initiators, or absorption of photons. Free-radical polymerization, however, is seldom quantitative: the resulting gel usually contains significant amounts of unreacted monomers, initiator, and accelerators-some or all of which may be toxic, and the reaction itself may be very exothermic. For ophthalmic applications in particular the requirements are stringent, and include a narrow range of reaction temperatures very close to ambient, optically clear material, very low chemical and photo-toxicity, and long-term stability in a wet, oxygenated, and photon-rich environment. The aim of the present invention in forming in situ gels is to develop new vitreous substitutes and injectable intraocular lens materials.

Accommodation is a dynamic process by which the refractive power of the optical system, principally the lens, is automatically adjusted to focus light on the retina. This ability is significantly decreased, usually by the fourth decade of life, and lost almost completely by the seventh decade of life through a progressive change in the volume and the elasticity of the lens resulting in an inability to focus on objects closer than arms length, a condition called presbyopia. Evacuating the capsular bag's contents and refilling it with and appropriate volume of a suitable material also offers a potential to restore accommodation to the presbyopic patient. Development of surgical procedures to evacuate the lens capsular bag through a small opening and identification of a suitable material to re-fill the capsular bag has been investigated. Such materials preferably have several advantages, including restoration of accommodation, a smaller corneosoleral incision than now required for semirigid replacement lenses, improved physiological positioning of the intraocular lens, and reduced rate of secondary opacification.

Both physical and chemical crosslinks for forming gels within the capsular bag have been exploited. For instance, Kessler (Experiments in refilling the lens. *Arch. Ophthalmol.* 71:412-417, 1964) used Carquille's immersion oil, silicone fluids, and damar gum to form physically crosslinked gels in rabbit eyes. Formation of gels by chemical crosslinking was popularized by Parel et al. (Phaco-Ersatz: Cataract surgery designed to preserve accommodation. *Graefes Arch. Clin. Exp. Ophthalmol.* 224:165-173, 1986), who utilized filler-free divinylmethylcyclosiloxane elastomer that typically cured within several hours at room temperature. Nishi et al. (Accommodation amplitude after lens refilling with injectable silicone by sealing the capsule with a plug in primates. *Arch. Ophthalmol.* 116:1358-1361, 1998) used polymethyldisiloxane containing hydrogen polysiloxane as a crosslinking agent. Others reported endocapsular polymerization in which a mixture containing monomers was injected and photopolymerized in situ to form the gel. Jacqueline et al. (Injectable intraocular lens materials based upon hydrogels, *Biomacromolecules* 2:628-634, 2001) recently reported the endocapsular photopolymerization of acrylate-modified N-vinylpyrolidone/vinylalcohol copolymer using an acrylamide-based photoinitiator, and identified some of the compositions to be dimensionally stable and optically clear. The toxicity, however, of unreacted monomers, and the exothermic nature of the polymerization reaction, makes the system impractical. Further, in all of the above cases, the mechanical properties of the refilling materials were not investigated. Neither were these chemically crosslinked gels reversible, thus making retrieval of the lens quite challenging.

In our previous work, we synthesized, characterized, and performed endocapsular polymerization with simultaneous gelation using polyethyleneglycol acrylates as a prototypic macromonomer. The extent of conversion during polymerization was approximately 95%, as is typical of most free-radical reactions. To address the issue of toxicity of the residual monomers, we quantitatively investigated the structure-toxicity relationship and observed that 1) acrylates were generally more toxic than methacrylates; 2) hydrophobic monomers were more toxic than hydrophilic ones in both classes; and 3) the mechanism of toxicity was probably from the ability of residual monomers to cross the lipid bilayer and subsequently react via Michael addition with intracellular proteins and DNA. We also observed that acrylate or methacrylates containing hydrophilic hydrogels were hydrolytically unstable in tissue culture medium. It is our continuing intention to identify and develop new techniques that will further our understanding of the use of polymers in ophthalmology, particularly as they influence accommodation and presbyopia.

In this context, we extend and explore the redox chemistry of thiols which nature employs for stabilizing the highly ordered structure of proteins. The use of disulfide reduction in the synthesis of reversible (solubilizable) hydrogel was first reported for preparing reversible polyacrylamide gel electrophoresis. More recently, this chemistry has been extended to the preparation of solubilizable hydrogel for validating theoretical formulations in network properties of hydrogels and for the entrapment of islets cells in designing bioartificial pancreases. However, this unique chemistry, that can potentially provide a route for introducing monomer-free compositions and can gel by chemical crosslinking with minimum production of heat and under physiological conditions (ambient temperatures, in presence of oxygen, and at near-neutral pH), has not been exploited for in situ for ophthalmic and dermatological application, such as forming injectable intraocular material and wound treatment. Therefore, the present invention provides a novel reversible hydrogel system that can interchangeably be converted from solution to hydrogel and vice versa at normal physiological pH and temperature without the toxicity of the prior art. The reversible hydrogel system of the present invention is particularly useful in refilling lens capsular bag and as vitreous substitute. The reversible hydrogel system is also useful in dermatological application, such as covering wounds and/or delivering drugs via the dermal route.

SUMMARY OF THE INVENTION

The reversible hydrogel systems of the present invention is reversibly converted between a hydrogel state and a solution by oxidation/reduction or by different wavelengths of light. The hydrogel can be reduced to form the solution; and the solution can be oxidized to form the hydrogel. Thus, the system is reversibly converted between a hydrogel and a solution.

The reversible hydrogel system of the present invention includes a copolymer that is formed by polymerization of the a monomer with a crosslinker. The crosslinker provides disulfide linkages within the copolymer molecule to form a hydrogel. When the hydrogel is reduced, the disulfide linkages are broken to yield a soluble copolymer solution. On the other hand, the copolymer solution can be oxidized to form disulfide linkages to reform the hydrogel. The oxidation is achievable at physiological pH of about 7.0 to about 7.4.

The hydrogel systems of the present invention can be used to form artificial lens by removing the lens content to produce an empty capsular bag, refilling the empty capsular bag with a solution of the copolymer, and oxidizing the solution in situ. The refractive index and other physical properties of the hydrogel can be reproduced by controlling the concentration of the copolymer in the solution and/or the degree of crosslinking in the hydrogel, and/or incorporating appropriate additives, such as particles, preferably nanoparticles. In some application, it is desirable to have drugs incorporated into the hydrogel forming the lens, such as those for intraocular pacification.

The hydrogel systems of the present invention can be used to form vitreous substitute by filling the eye with an appropriate volume of the copolymer solution and oxidizing the solution in situ.

The hydrogel systems of the present invention are also useful in dermatological application. In an embodiment, a sterile solution of the copolymer can be applied to the wound and allowed to gel. The copolymer solution can contain medications and UV absorbent, such as antibiotics, to keep the wound sterile and to accelerate healing.

BRIEF DESCRIPTION OF THE DRAWINGS

FIG. 5 shows oxidative regelation of thiol containing ABSH polymers via a) air oxidation at alkaline pH; and b) thiol disulfide exchange reaction.

DETAILED DESCRIPTION OF THE PREFERRED EMBODIMENT

The hydrogel systems of the present invention contains a copolymer that is a hydrogel in oxidized state and is in a solution in reduced state. The copolymer is preferably obtained by copolymerizing a monomer with a crosslinker. The crosslinker provides intermolecular crosslinkages to form the hydrogel. The monomer can be acrylamide, N-ornithine acrylamide, N-(2-hydroxypropyl)acrylamide, hydroxyethylacrylate, hydroxyethylmethacrylate, polyethyleneglycol acrylates, polyethyleneglycol methacrylates, N-vinyl pyrolidone, N-phenylacrylamide, dimethylaminopropyl methacrylamide, acrylic acid, benzylmethacrylamide, methylthioethylacrylamide, or combinations thereof Polymers with functional groups that can be modified or derivatized to incorporate disulfide groups or reversible crosslinks may also be appropriate for the present invention.

The polymer preferably includes crosslinkable groups which are capable of forming covalent bonds within the polymer or with other polymers while in aqueous solution, which permit crosslinking of the polymer to form a gel, either after, or independently from thermally or photochemically dependent gellation of the macromer. Chemically or ionically crosslinkable groups known in the art may be provided in the macromers. The preferred crosslinkable groups are unsaturated groups including vinyl groups, allyl groups, cinnamates, acrylates, diacrylates, oligoacrylates, methacrylates, dimethacrylates, oligomethoacrylates, or other biologically acceptable photopolymerizable groups. The crosslinker is preferably a disulfide linker, such as N, N'-bis(acryloyl)cystamine (BAC). Other useful crosslinkers include, but is not limited to, methylenebisacrylamide, methylenebismethacrylamide, esters of unsaturated mono- or polycarboxylic acids with polyols, such as diacrylate or triacrylate, e.g., butanediol diacrylate, butanediol dimethacrylate, ethylene glycol diacrylate, ethylene glycol dimethacrylate and also trimethylolpropane triacrylate, allyl compounds such as allyl (meth)acrylate, triallyl cyanurate, diallyl maleate, polyallyl esters, tetraallyloxyethane, triallylamine, tetraallylethylenediamine, pentaerythritol triallyl esters or allyl esters of phosphoric acid and also vinyl compounds such as vinyl acrylate, divinyl adipate, divinylbenzene and vinylphosphonic acid derivatives. Other non-reversible linkers can be included in the polymer to form branches.

Photochemically reversible linker appropriate for the present invention can include, but is not limited to, stilbene, azo, and cinnamoyl derivatives. With photochemically reversible linkers, gellation of the copolymer occurs at a particular wavelength, while liquefaction of the copolymer occurs at a different wave length. For example, the copolymer solution forms a hydrogel by exposure to a first wavelength; and the hydrogel reverts to a copolymer solution by exposure to a second wavelength.

Figure 1:
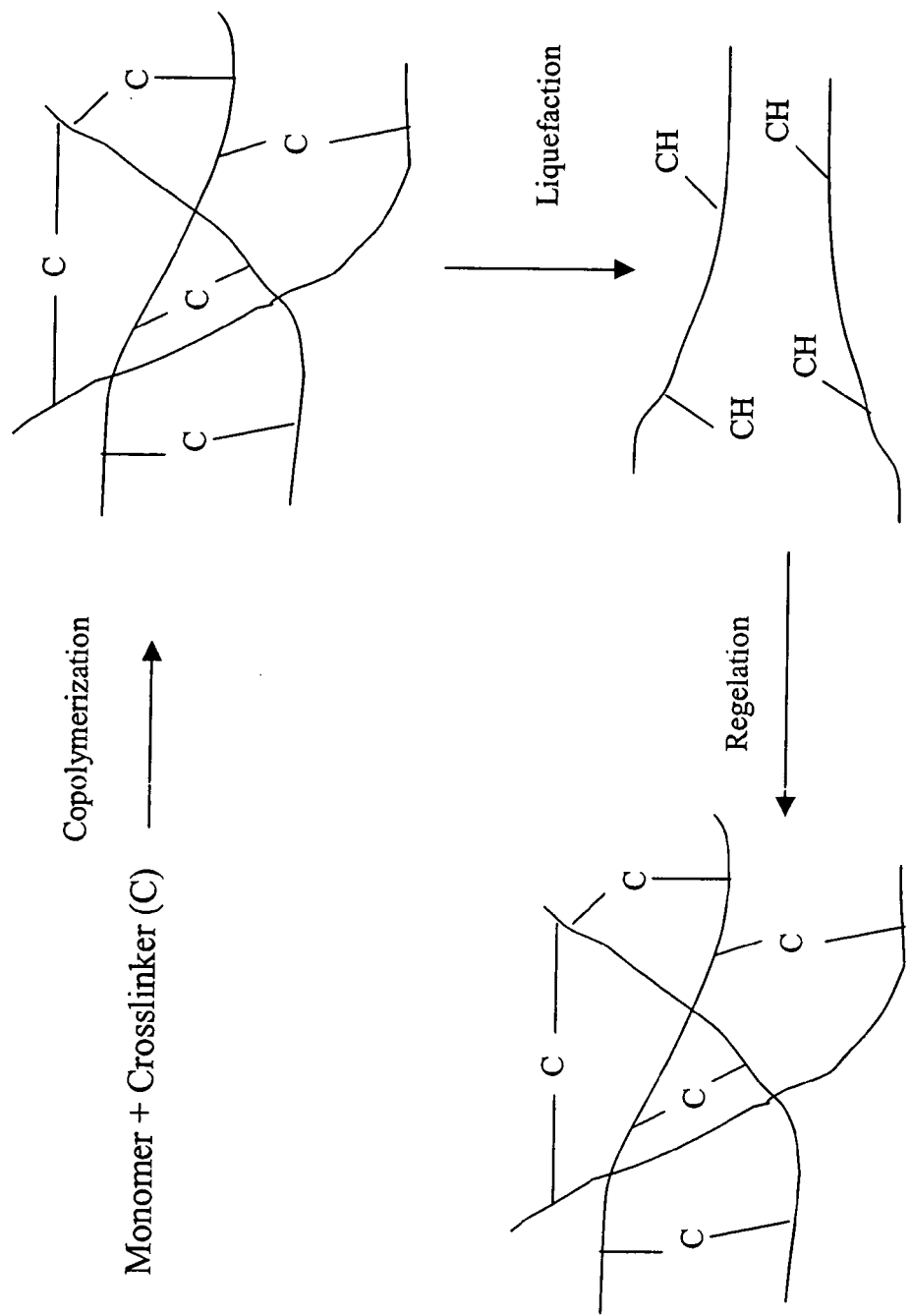
FIG. 1 shows the general process of the making the reversible hydrogel system.

FIG. 1 shows a schematic of the formation of the hydrogel, solubilization of the copolymer, and reformation of the hydrogel. The copolymerization of the monomer with the linker formed a crosslinked hydrogel. The polymerization is initiated with water-soluble or monomer-soluble initiators or redox initiator combinations. Examples of water-soluble initiators are the sodium, potassium and ammonium salts of peroxodisulfiric acid, hydrogen peroxide, tert-butyl peroxide, tert-butyl hydroperoxide, potassium peroxodiphosphate, tert-butyl peroxypivalate, cumyl hydroperoxide, isopropylbenzyl monohydroperoxide and azobisisobutyronitrile. Examples of monomer-soluble initiators are diacetyl peroxydicarbonate, dicyclohexyl peroxydicarbonate and dibenzoyl peroxide. The initiators are generally used in an amount of 0.01 to 0.5% by weight, based on the total weight of the monomers. Combinations of said initiators in combination with reducing agent(s) may be used as redox initiators. Suitable reducing agents can be, but are not limited to, the sulfites and bisulfites of alkali metals and of ammonium, for example, sodium sulfite, derivatives of sulfoxylic acid such as zinc or alkali metal formaldehyde sulfoxylates, for example sodium hydroxymethanesulfonate, and ascorbic acid. The amount of reducing agent is preferably 0.01 to 0.5% by weight, based on the total weight of the monomers.

Once the copolymer is formed, it is preferably washed to completely remove unreacted monomers and crosslinkers. The washing step is especially preferred for monomers that are toxic to human use. For example, acrylamide is known a carcinogen and neurotoxin; however, its polymer, polyacrylamide, is harmless. Thus, after polymerization of acrylamide, it is highly desirous that the unreacted acrylamide is completely washed from the hydrogel. After removal of unreacted monomers and crosslinkers, the copolymer can be further swollen by a liquid, preferably water, to obtain the desired water content.

The hydrogel can be liquefied to form a solution of the copolymer by disruption of the crosslinkages. In the case of disulfide linkages, liquefaction can be accomplished by chemically reducing the hydrogel so that the disulfide linkages are reduced to thiols. Reduction preferably takes place in the presence of a reducing agent, such as dithiolthreitol (DTT). Other reducing agents can be, but are not limited to, of 2-mercaptoethanol, dithioerythritol, cystein, butanethiol, sodium borohydride, cyanoborohydride, mercaptoethylamine, ethylmaleimide, and tri(2-carboxyethyl)phosphine hydrochloride (TCEP.HCl). The reducing agent is selected based on the nature of the crosslinkage. For disulfide linkages, DTT is the preferred reducing agent. Once reduced, the hydrogel liquefies and becomes a copolymer solution. In the case of copolymers having disulfide bonds, reduction results in the thiols containing copolymers that are water soluble. The copolymer solution can be diluted, concentrated and/or dried as desired. For storage, the copolymer is preferably precipitated from solution, for example by methanol, filtered, and dried. Other methods, including freeze drying, are also appropriate. The stored copolymer solids that can subsequently be dissolved in a solution to desired concentrations for use.

The hydrogel can be reformed from the copolymer solution by reforming the crosslinkages within the copolymer molecule. In the case of disulfide linkages, regelation can be accomplished by oxidization of the copolymer solution, preferably in the presence of an oxidizing agent, preferably atmospheric oxygen. Although atmospheric oxygen is preferred, other oxidizing agent, such as dithiodipropionic acide (DTDP), cystamine, 2-hydroxyethyldisulfide hydrogen peroxide, organic peracids, peroxy carbonates, ammonium sulfate peroxide, benzoyl peroxide, perborates, and the like, can also be used. Importantly, however, the preferred oxidizing agents should have no significant toxicity to human and/or animals.

With polymers using photochemically dependent linkers such as stilbene, azo, and/or cinnamoyl derivatives, regelation is accomplished by exposing the copolymer solution to light at an appropriate wavelength. Liquefaction of the gel can thus be accomplished by exposing the gel to light at an appropriate wavelength, usually one that is different from the gelation wavelength.

Without further description, it is believed that one of ordinary skill in the art can, using the preceding description and the following illustrative examples, make and utilize the compounds of the present invention and practice the claimed methods. The following example is given to illustrate the present invention. It should be understood that the invention is not to be limited to the specific conditions or details described in this example.

Example 1

Acrylamide/BAC Hydrogels

Experimental Methods
Synthesis of Polyacrylamide/BAC Hydrogels

Varying compositions of hydrogels were synthesized by reacting acrylamide (Aam) with BAC at acrylic mole ratios of 98/2, 96/4, and 94/6 at 5% (w/w) in 25% ethanol (25:75=ethanol:water v/v). Nitrogen was bubbled through the solution for about 30 minutes to displace any dissolved oxygen prior to the initiation of the polymerization. The reaction was initiated by adding 2.1% (w/w) of TEMED and 0.4% (w/w) of APS and allowed to proceed for 15 hours at 25° C. Aqueous ethanol was used as solvent because of the limited solubility of BAC in water. The resulting gels were removed from the beaker, swelled in 500 mL of water for two days, crushed into small pieces, and washed with distilled water. The gels from the above copolymer compositions were labeled as ABSS2, ABSS4, and ABSS6, indicating that they contained disulfide (—SS—) bonds by incorporating 2, 4, and 6 acrylic mole % of BAC, respectively.
Reductive Liquefaction of Monomer-Free Swollen Hydrogels The gels were crushed into small pieces and liquefied by adding DTT, at 10 mol/mol of BAC, at pH 7.0. Nitrogen was bubbled through the solution under stirring while the reduction was carried out for two, four, and six hours for ABSS2, ABSS4, and ABSS6, respectively. After the gels were completely dissolved, the solution was acidified to pH 3 using 10% (v/v) HCl and precipitated in excess methanol under vigorous stirring. The precipitated —SH polymer was filtered, dried under vacuum, and stored under reduced pressure until needed. The above soluble polymers from ABSS2, ABSS4, and ABSS6 were labeled as ABSH2, ABSH4, and ABSH6 respectively, indicating that they now contained —SH groups instead of disulfide bonds.
Characterization of the Soluble Copolymers The thiol (—SH) content of each copolymer was determined using Ellman's reagent. Briefly, 50 µL of 0.5% (w/v) copolymer solution (pH 4, nitrogen bubbled) was added to a mixture of 50 µL of 0.01 M Ellman's reagent (in 0.1M phosphate buffer, pH 8.0), 500 µL of 0.1 M phosphate buffer (pH 8), and 450 µL of distilled water. Absorbance (using Beckman DU54 spectrophotometer) of the resulting solution at 412 nm was determined five minutes after mixing. The concentration of the —SH in each ABSH polymer was calculated using the molar absorptivity of 13,600 $M^{-1}$ $cm^{-1}$.

Molecular weights of the reduced polymers were determined using a Viscotek HPLC-GPC system (Houston, Tex.) equipped with static light scattering and refractive index detectors in tandem with a viscosity detector. The stationary phase consisted of a dual column of G6000PWXL and G4000PWXI. (Tosoh Biosep, Montgomeryville, Pa.), connected in series, and the mobile phase was 20 mM Bis-Tris buffer (pH 6.0, 0.1% sodium azide). Samples were prepared in water (pH 4, $N_2$ saturated) at a concentration of 0.5% (w/v). Polyethylene glycol standards (Viscotek, Houston, Tex.) of molecular weight (Mw) 1000 to 950,000 were used for calibration.

The presence of thiol groups in the soluble polymers and their disappearance on regelation was investigated by Raman spectroscopy (Kaiser Holoprobe Series 5000 Raman spectrophotometer, operating at the Argon laser wavelength of 514 nm). Aqueous polymer samples, in a vial, were directly exposed to the laser beam, and spectra were acquired at a resolution of 2 $cm^{-1}$. A custom-built sample holder was utilized on the commercially available translation stage to allow reproducible placement of samples with respect to laser focus. The spectra were analyzed using the GRAMS/32 software package (Galactic Industries Corporation, Salem, N.H.).

Regelation of copolymer solutions was performed using DTDP (details given below), after which the gel was swelled for two days. The swollen gel, after washing with water several times, was used for the Raman experiments to observe the disappearance of the peak for —SH moiety and the appearance of a peak corresponding to the formation of the disulfide (—S—S—) bonds.
Regelation of Copolymeric Aqueous Solution Three different concentrations (% w/v) of polymer solutions, in nitrogen saturated water at pH 4, were prepared from each of the reduced polymers: 10.0, 12.5, and 15.0% from ABSH2; 5.0, 7.5, and 10.0% from ABSH4; and 2.0, 3.0, and 4.0% from ABSH6. Polymer solutions (1 mL each) were placed in test tubes and the pH of the solutions were adjusted to approximately 7.4 using calculated amounts of 10 M NaOH, followed by the addition of the required amounts of DTDP (0.5M, pH 7) and vigorous stirring. An equimolar amount of DTDP, based on the —SH content of each ABSH polymer solution, was added. Gelation was observed visually by tilting the tube. To evaluate the ease of injection and uniformity of the gel within a capsular bag, a special mold, mimicking the natural pig lens, was used.

Figure 2:
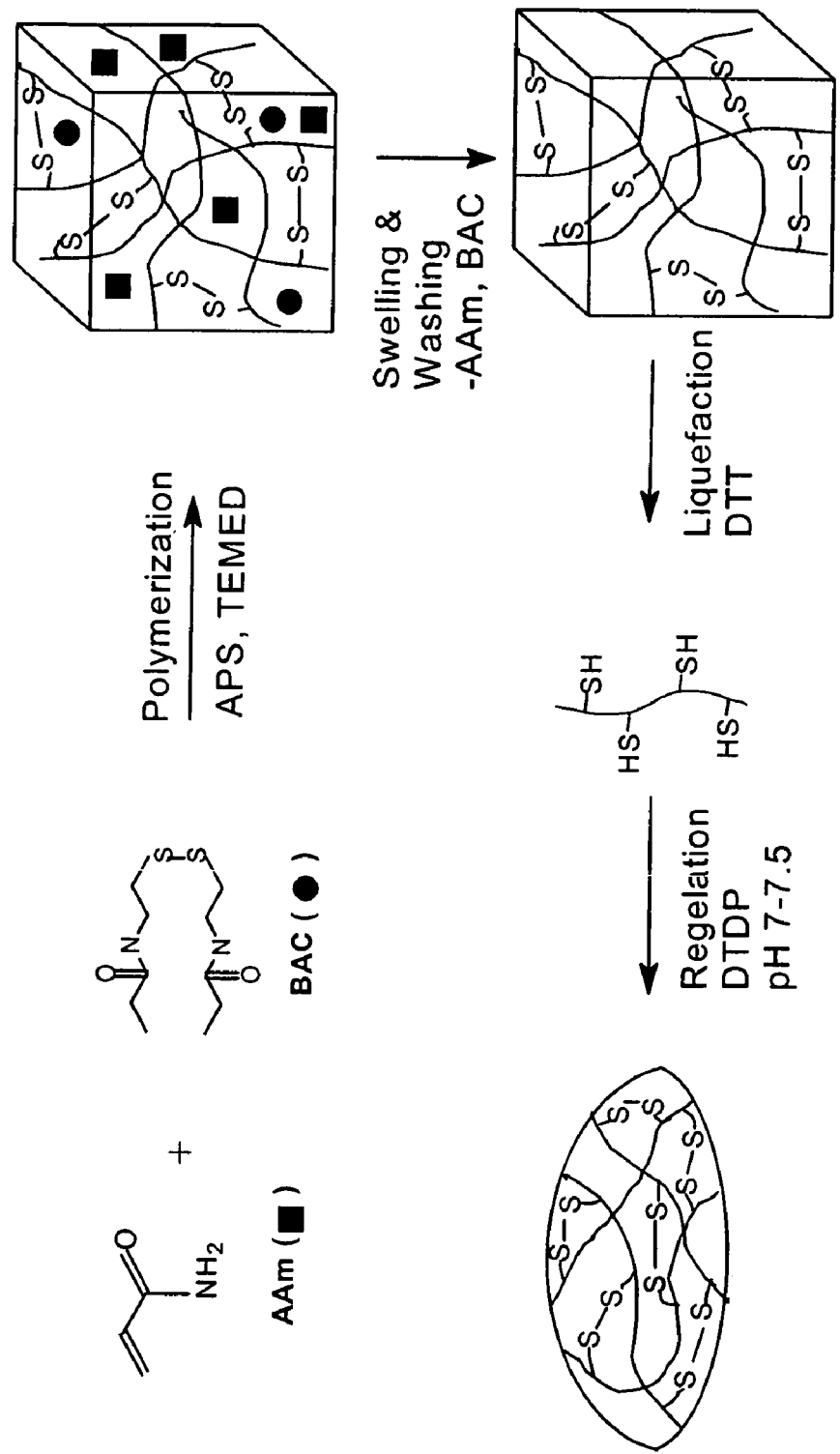
FIG. 2 shows the schematic of the preparation of the polyacrylamide/BAC reversible hydrogel system.
Figure 3:
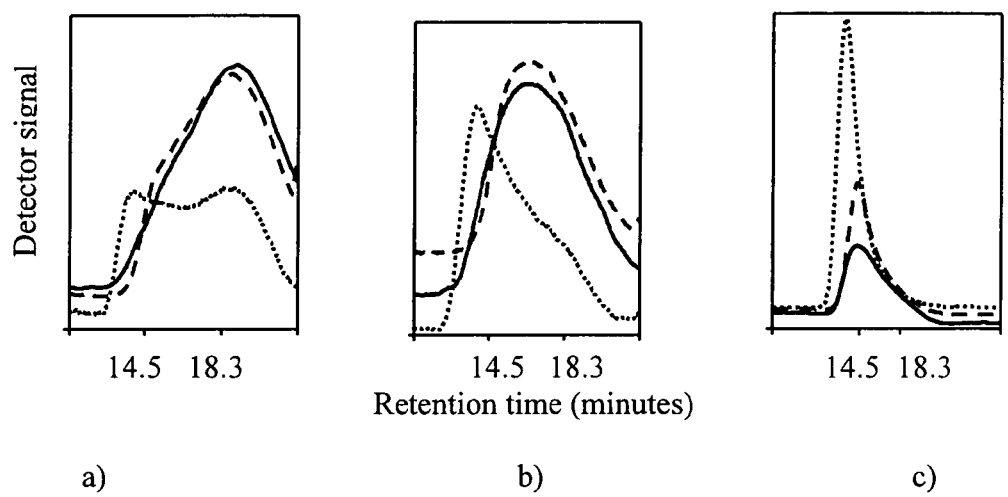
FIG. 3 shows the HPLC-GPC triple detector chromatograms of ABSH2 (continuous line), ABSH4 ( - - - ) and ABSH6 ( . . . ) polymers. Signals are from a) RI; b) viscosity; and c) light scattering detectors.

Preparation of cylindrical-shape gels was carried out using a Teflon mold. The static moduli of the re-gelled samples (as cylinders or thin discs) were determined from stress/strain experiments using a dynamic mechanical analyzer (Perkin Elmer DMA7e, Norwalk, Conn.) and the analyses were completed no less than one hour after the addition of DTDP. A static stress scan was performed from 0 to 25 mN at a rate of 5 mN/min at 25° C. Preparation of copolymeric hydrogels and their reduction and regelation from water-soluble copolymer are schematically shown in FIG. 2.
Endocapsular Gelation Copolymer solutions (% w/v) of 10.0 and 12.5% from ABSH2; of 5.0 and 7.5% from ABSH4; and of 2.0% from ABSH6, respectively, were evaluated for endocapsular gelation. Freshly enucleated pig eyes were purchased from a local abattoir shortly after slaughter. Typically, each eye was stabilized on a styroform board; the cornea and iris were removed. A capsulotomy of from 1.0 to 1.2 mm diameter near the equator on the anterior capsular bag was performed using an Ellman Surgitron instrument (Edmonton, N.J.). The capsular bag was then evacuated using a Storz Phacoemulsification ultrasound instrument (Premiere, Bausch and Lomb, St, Louis, Mo.). DTDP was added to copolymer solution and mixed well just prior to injection. In a typical instance, 800 µL of 5% (w/v) solution of ABSH4 (pH adjusted to 7.4 using 10M NaOH) was placed, in a test tube and, 43 µL of DTDP (0.5 M, pH 7.0) was added and mixed thoroughly for 10 seconds in a vortex stirrer and drawn up in a syringe with a needle of 1.0 mm outer diameter, the tip of which was attached to a cone-shaped plastic microtip. The copolymer was injected carefully and quickly into the bottom of the capsular bag, which was thus filled without bubbles, and held closed for the next two to three minutes. The gelation usually occurred within three minutes. The surgical method of injection and re-gelation of the hydrogels are schematically represented in FIG. 3.

Results

Synthesis of Poly(AAm-co-BAC) Hydrogels

Three different hydrogels of varying compositions were prepared from acrylamide and BAC at 2, 4, and 6 acrylic mole % of BAC with respect to acrylamide. As expected, increasing the BAC resulted in gels with better structural integrity. Gels having higher amount of BAC were slightly less transparent. ABSS2 did not form a stable gel but a viscous solution instead; however, stable gels were obtained at higher concentrations (>15%).

Synthesis and Characterization of ABSH Copolymers

The key step in obtaining water-soluble copolymers (ABSHs) from the crosslinked gels (ABSHs) involved the complete reduction of disulfide bonds (—S—S—) into thiol (—SH) groups, as shown in FIG. 2. Reduction of the gels by DTT resulted in almost complete reduction (as shown by the —SH content values in Table 1) of the disulfide bonds. Dissolution of the gels was significantly accelerated if nitrogen was bubbled through the solution. The —SH content of the water-soluble copolymers (ABSHs) is proportional to the BAC concentration used in the copolymerization, as shown in Table 1.

TABLE 1

| Gel Name | AAm/BAC (acrylic mole %) | —SH content ($\times 10^{-4}$ moles/g) Calculated | —SH content ($\times 10^{-4}$ moles/g) Determined | Mean Mw ($\times 10^5$ D) |
|---|---|---|---|---|
| ABSS2 | 99/2 | 2.76 | 2.22 | 2.8 |
| ABSS4 | 98/4 | 5.44 | 5.37 | 4.28 |
| ABSS6 | 97/6 | 8.03 | 7.94 | 18.60 |

FIG. 3 shows the GPC traces of ABSH copolymers observed by the three detectors of the HPLC-GPC. Increasing the BAC content in the copolymerization increases the molecular weight and leads to broader molecular weight distribution, as shown in FIG. 3, trace a. The results of the weight-average molecular weight (Mw) of ABSH polymers are shown in Table 1.

Figure 4:
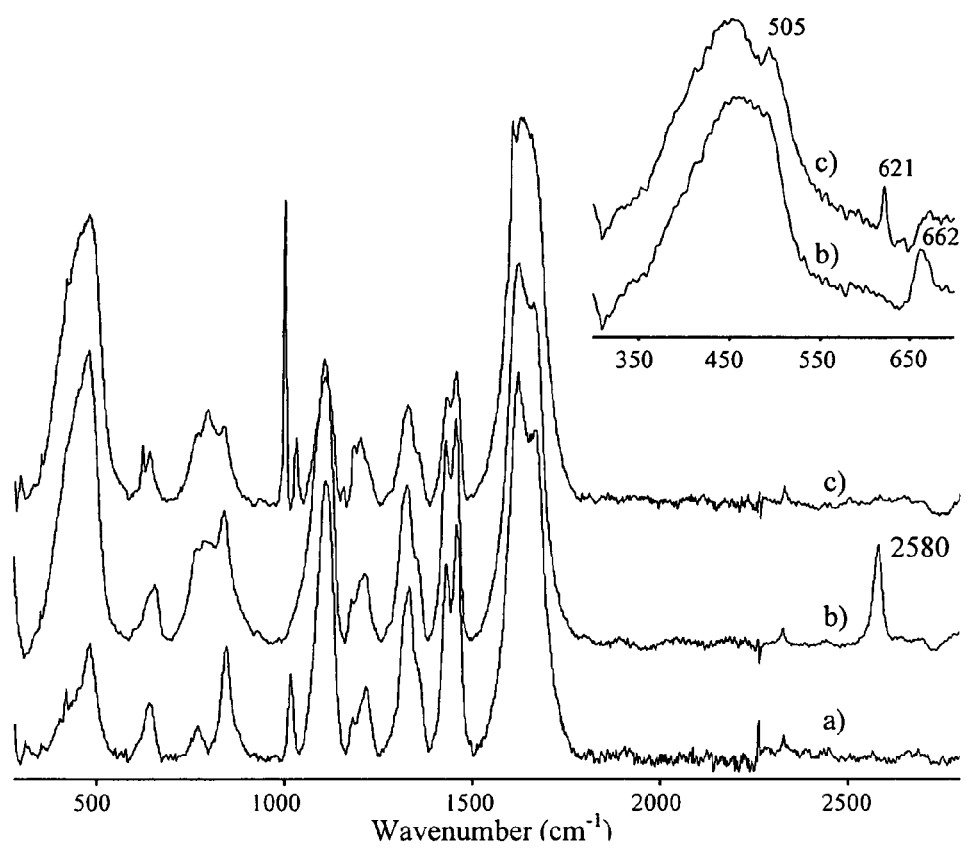
FIG. 4 shows the Raman spectra of a) 4% (w/v) aqueous solution of ABSH6 before gelation; b) 4% (w/v) aqueous solution of ABSH6 after gelation; and c) 5% (w/v) aqueous solution of polyacrylamide (prepared using the same experimental condition without BAC). Insert shows the expanded region of b) and c) after a) is subtracted.

Presence of thiol and its disappearance on regelation, with concurrent formation of disulfide (—S—S—) bonds, was confirmed by Raman spectroscopy. The Raman spectra of ABSH6 (4 w/v % aqueous solution) and its corresponding reformed gel, RABSS6 (the "R" indicating the reformed gel from ABSH6) are shown in FIG. 4. The characteristic absorption at 2580 cm$^{-1}$ corresponds to the —SH stretching vibration ($v_{SH}$), noted as trace b in FIG. 4, which disappeared completely upon gelling. The absorption corresponding to —S—S— stretch ($v_{S—S}$) usually appears at about 510 cm$^{-1}$, provided it does not overlap with any other vibration. Since the polymer is mostly polyacrylamide, it was difficult to observe the $v_{S—S}$ distinctly at $v_{S—S}$, noted as trace c in FIG. 4, because of interference from a broad, unsymmetrical —C—C— skeletal deformation peak of polyacrylamide centered at 485 cm$^{-1}$. This problem was resolved by subtracting the spectrum of polyacrylamide (trace a in FIG. 4, prepared using the same procedure, but without BAC) from the spectrum of the RABSS6. As shown in the insert of FIG. 2, the $v_{S—S}$ was clearly observed as a shoulder peak at 505 cm$^{-1}$.

In addition to the —SH and —S—S— vibrations, the peak positions of —C—S— stretch ($v_{C—S}$) from the —C—S—H moiety in ABSH6 and from —C—S—S—C— in RABSS6 were also observed distinctly at 662 cm$^{-1}$ and 621 cm$^{-1}$, respectively, after the subtraction of polyacrylamide spectrum, as shown in the insert of FIG. 4. In addition to the above characteristic absorptions, the other absorption peaks shown in FIG. 4 correspond to the Raman spectra of polyacrylamide (Gupta et al. Laser Raman spectroscopy of polyacrylamide. *J. Polym. Sci., Polym. Phys. Edn.* 19:353-360, 1981).

Regelation and Mechanical Properties

Regelation of ABSH polymers can be achieved by air oxidation of thiol or by thioldisulfide exchange reaction (FIG. 5). The reaction rate of one electron transfer from ABS$^-$ ion (from ABSH) to oxygen determines the rate of air oxidation of the thiol. This reaction rate increases with increasing pH. At pH 7.4, gelation usually occurred within 12 hours. Hisano et al. (Entrapment of islets into reversible disulfide hydrogels. *J Biomed Mater Res.* 40:115-123, 1998) reported that air oxidation took about six hours to form the gels at pH 8.8 for similar types of thiolated acrylamide polymers. Unlike air oxidation, the thioldisulfide exchange reaction resulted in gelation within a few minutes at pH between 7.0 and 7.5, which is closer to physiological pH. Since the gelation times were so short (all less than five minutes), we were able to carry out regelation experiments for several different concentrations of ABSH polymers. The concentrations of ABSH polymers and the static moduli of the re-gelled specimens are tabulated in Table 2. The modulus of gels formed at the same concentration increases with increasing molecular weight and —SH content. All of the reformed gels were transparent.

TABLE 2

| Gels from | Concentration from ABSH copolymers (% w/v) | | | | | | | |
|---|---|---|---|---|---|---|---|---|
| | 2 | 3 | 4 | 5 | 7.5 | 10 | 12.5 | 15 |
| | Modulus (KPa) | | | | | | | |
| ABSH2 | — | — | — | — | — | 0.333 | 0.800 | 0.786 |
| ABSH4 | — | — | — | 0.393 | 0.590 | 1.10 | — | — |
| ABSH6 | 0.385 | 0.467 | 0.556 | — | — | — | — | — |

In the present work, gelation occurred in less than 30 seconds for 15% solution of ABSH2, 10% solution of ABSH4, and 3 and 4% solutions of ABSH6. Because of the high viscosity and rapid gelation, however, endocapsular gelations were not attempted using these samples. Instead, air oxidation was the preferred technique. The lower concentrations, which are not included in Table 2, were not suitable for forming stable gels. Overall, the rate of gelation is a function of the oxidizing agent, pH and light.

Endocapsular Relation

Figure 6:
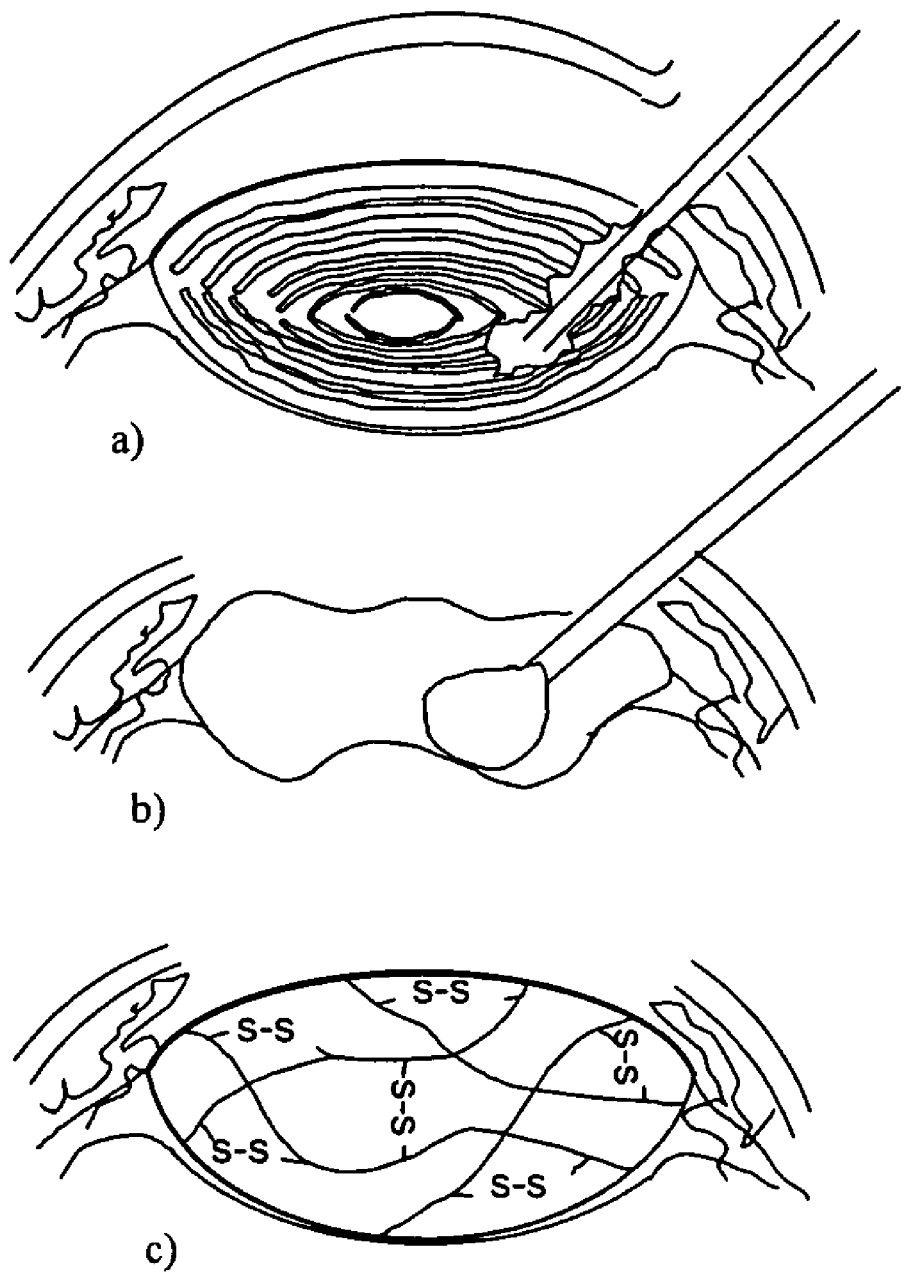
FIG. 6 shows a schematic of the surgical procedure for endocapsular hydrogel formation: a) perforation of the cornea and retraction of the iris, followed by the removal of the lens content; b) refilling the empty lens capsular bag with a solution of the reversible hydrogel material; and c) in situ regelation of the reversible hydrogel material.

The suitability of water-soluble copolymer solution (ABSHs) for endocapsular gelation was demonstrated in pre-evacuated porcine lens capsular bags. As stated earlier, very rapid re-gelation prevented testing of several polymer concentrations. Endocapsular gelation was performed using 10.0 and 12.5% solutions of freshly prepared ABSH2, 5.0 and 7.5% solutions of ABSH4, and 2.0% solution of ABSH6. In all these cases, regelation occurred within five minutes. Thanks to the high initial viscosity, which progressively, increased upon addition of DTDP, leakage during refilling did not occur. The surgical procedure of in-vitro refilling for endocapsular gelation is schematically represented in FIG. 6. Here, the cornea was perforated and the content of the lens was removed by phagofragmentation resulting in an empty capsular bag. The empty capsular bag was then refilled with the appropriate ABSH solution and regelled in situ.

Figure 7:
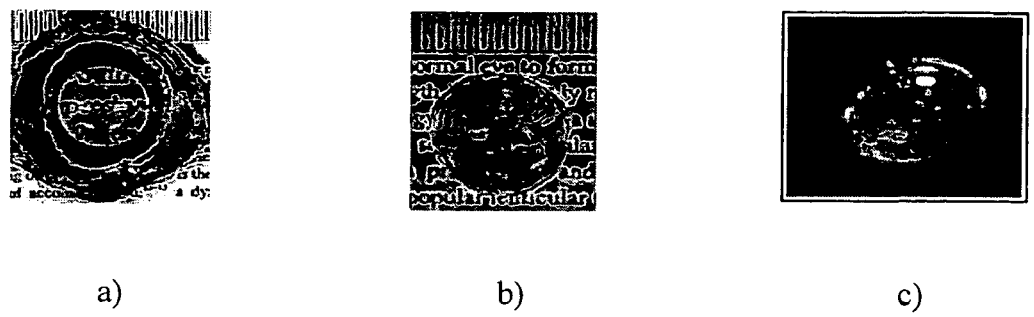
FIG. 7 shows re-gelled sample of 10 w/v % ABSH4 a) inside the porcine lens capsular bag; b) explanted from the lens capsular bag; and c) prepared in a mold.

FIG. 7a shows a representative porcine eye sample where endocapsular gelation was carried out with a 10% (w/v) solution ABSH4. Objects viewed through the lens appeared clear and undistorted. FIG. 7b shows the re-gel lens explanted from the porcine lens capsular bag. Formation of uniformly transparent gels was also verified in molds shaped in the form of a lens (FIG. 7c).

Discussion

The primary aim of this work is to demonstrate the feasibility of using thiol containing copolymers as injectable precursors for in vivo chemical crosslinking under physiological conditions (ambient temperature, in the presence of oxygen, and at near-neutral pH). It is possible to form, in pre-evacuated capsular bags, optically clear gels whose modulus was approximately that of the youthful lens substance (~1000 Pa). The gelling chemistry uses the facile oxidation of pendant thiols to disulfide by slow air oxidation or the rapid exchange reaction mediated by suitable, non-toxic disulfide reagents. Such system is free of toxic monomers, does not involve exothermic reactions close to the living tissues, is leak-free, and has a rate of gelling that can be modulated by appropriate biocompatible accelerators and photons.

Here, polyacrylamide is used as a model scaffold or backbone structure and may be replaced by any polymer chain. Incorporating hydrophobic moieties can significantly enhance the solution property of the copolymer, i.e., viscosity and/or thixotropy. Additionally, thiols could be either pendant or at chain ends in a multi-armed polymer. The chemistry is also applicable to thiol-containing silicones, which have unusually high oxygen permeability. Because hydrophilic, water-swellable acrylates are usually biodegradable and not suitable for long-term use as vitreous substitutes or intraocular lens material, acrylamide derivatives are chosen for their generally greater hydrolytic stability. Another distinct advantage of this system is that the initial formation of a network outside the body facilitates the removal of heat as well as monomers and other toxic chemicals, problems that otherwise severely limit in vivo polymerization. The reduction of disulfide bonds in the hydrogel using DTT to obtain water-soluble ABSH copolymers is an important step that is influenced not only by the redox potential of the reducing agent, but also by concentration, time, pH, and nitrogen atmosphere. After considering these factors, it is found that using 10 molar excess of DTT and stirring under nitrogen to be most suitable approach for obtaining copolymers for endocapsular regelation. Use of acidified methanol (pH 3) during precipitation of the polymer was critical to maintaining the thiols in the reduced state during subsequent processing. Otherwise, the copolymers are only partly soluble. Upon drying, the samples were kept under reduced pressure until further use. As seen from the —SH content in Table 1, it is possible to reduce the disulfide bonds almost quantitatively. The gel can be reformed through either simple air oxidation or thiol-disulfide exchange reaction by adding DTDP. While the —SH content, concentration, and molecular weight of the copolymer influenced the regelation characteristics and moduli of the resultant gels, it is obvious from Table 2 that very high or low values of the above parameters render the material unsuitable for endocapsular gelation. In general, the modulus of the hydrogel increases with increasing —SH and copolymer concentration; and the hydrogel remains optically clear. Cystamine and 2-hydroxyethyldisulfide can also been used for regelation, but DTDP is less toxic than either of them.

In situ endocapsular hydrogel formation using reversible disulfide chemistry is a promising technique, not only for developing injectable intraocular lenses but also for use as vitreous substitutes, and topical medicaments. Unlike in situ polymerization and gelation, the reversible hydrogel system described here involves only in situ gelation, with no noticeable change in temperature. Because the copolymer is free of monomers and was injected at a concentration with a viscous consistency, toxicity from monomers and leakage is avoided. The time of regelation can be easily manipulated using DTDP, oxygen, pH, and/or photons.

Example 2

Acrylamide/BAC/N-phenylacrylamide Hydrogels

Copolymerization of acrylamide (AAm), bisacryloylcystamine (BAC), and N-nhenvyacrvylamide (NPA) was carried out at acrylic mole ratios of 94/4/2 at 5% (w/w) in 25% ethanol (25:75=ethanol:water v/v). Nitrogen was bubbled through the solution for about 30 minutes to remove any dissolved oxygen prior to the initiation of the polymerization. The reaction was initiated by adding 2.1% (w/w) of tetramethylethylenediamine and 0.4% (w/w) of ammonium persulfate and allowed to proceed for 15 hours at 25° C. Because of the limited solubility of BAC in water, aqueous ethanol was used as the solvent. The resulting gel was removed from the beaker, swelled in 500 mL of water for two days, crushed into small pieces and washed with distilled water. The copolymeric gel was labeled AB4N2SS indicating that it contained disulfide (—SS—) bonds by incorporating 4 acrylic mole % of BAC and 2 acrylic mole % of NPA.

The liquefaction of crushed gels (AB4N2SS) was achieved by the addition of dithiothreitol (DTT) (10 mol/mol of BAC used) to the crushed hydrogels. The reduction was carried out at pH 7.0 for 4 hours, while nitrogen was bubbled through the solution with stirring. After complete solubilization, the copolymer solution was acidified to pH 4 using 10% (v/v) HCl and precipitated in methanol (pH 4) with vigorous stirring. The precipitated —SH copolymer was filtered, dried under vacuum, and stored under reduced pressure at all times. The above obtained thiol containing water-soluble copolymer, from AB4N2SS was labeled AB4N2SH.

A 5% (w/v) solution of AB4N2SH was prepared in water ($N_2$ saturated) initially at pH ~4 and after the complete dissolution, the pH was adjusted to 7 using 7 μL of 5 M NaOH. Then, 162 μL of 0.5M DTDP (pH=7) was added to reform the hydrogel. The total volume of the composition was 3 ml. Similarly, 7%, 9%, and 11% (w/v) solutions of AB4N2SH were also prepared and used for the formation of hydrogels. The hydrogels were analyzed for their modulus values. The polymer solution (9, 11%) exhibited "honey-like" consistency, shear thinning when injected through the syringe, and almost instantaneously set within the pocine capsular bag as a physical gel without leaking. This physical gel was then transformed into a chemical gel.

| Regelled hydrogels | Concentration of AB4N2SH polymers (% w/v) | | | |
|---|---|---|---|---|
| | 5 | 7 | 9 | 11 |
| | Static modulus (Pa) | | | |
| RAB4N2SS | 375 | 428 | 734 | 1008 |

Example 3

Hydrogels as Vitreous Substitute

The copolymer (AB4SH) was prepared from the hydrogel obtained by polymerizing acrylamide with 4 acrylic mole % of bisacryloylcystamine (BAC). The detailed experimental procedure was similar to those described in Example 1.

Figure 8:
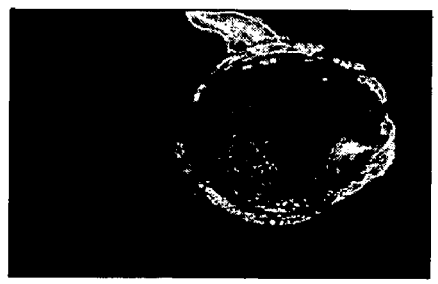
FIG. 8 shows a) vitreous substitute in human cadaver eyes seen after excision of the sclera, RPE, and retina; and b) eye dissected along the visual axis.
Figure 8:

A 7% (w/v) solution AB4SH was prepared in water ($N_2$ saturated) initially at pH ~4 and after the complete dissolution, the pH was adjusted to 7 using 15 µL of 1 M NaOH. After which, 62 µL of 0.5M DTDP (pH=7) was added. The total volume of the composition was 1 ml and injected into pre-evacuated human cadaver eye vitreous cavity. The in-situ gel equilibrated with the residual water in the vitreous cavity thus making the final composition of the gel inside the cavity substantially less than 7% (FIG. 8). However, in general, gels containing higher percentage of BAC require lower concentration to gel and preferable as vitreous substitute.

In the current studies, acrylamide is employed as a monomer to be copolymerized with BAC, but other acrylamides or vinylmonomers can also be used. This technique of introducing pendant thiols into the polymer, along with appropriate choice of the primary polymer, can be used to design gels for specific end uses. Although much effort has been spent to develop biocompatible hydrogels, this reversible hydrogel system has not been previously investigated for in situ medical applications. Collectively, these observations indicate that this system is novel.

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A method of forming a replacement intraocular lens in situ in an eye comprising the steps of
   a) introducing a reversible hydrogel system in solution into the capsular bag, wherein the reversible hydrogel system comprises a copolymer, wherein said copolymer is a hydrogel when in an oxidized state, and is a solution when in a reduced state, and wherein said copolymer is produced by polymerization of a monomer with a disulfide crosslinker, said monomer being selected from the group consisting of acrylamide, N-ornithine acrylamide, N-(2-hydroxypropyl)acrylamide, hydroxy-ethylacrylate, hydroxyethylmethacrylate, polyethyleneglycol acrylates, polyethyleneglycol methacrylates, N-vinyl pyrrolidone, N-phenylacrylamide, dimethylaminopropyl methacrylamide, acrylic acid, benzylmethacrylamide, and methylthioethylacrylamide; and
   b) gelling the reversible hydrogel system.

2. The method of claim 1, wherein the crosslinker is N, N'-bis(acryloyl)cystamine.

3. The method of claim 2, wherein the oxidization occurs at a pH of about 6.5 to about 7.5.

4. The method of claim 2, wherein the hydrogel is hydrophobic.

5. The method of claim 2, wherein the hydrogel is hydrophilic.

6. The method of claim 2, wherein the hydrogel is anionic.

7. The method of claim 2, wherein the hydrogel is cationic.

8. The method of claim 2, wherein the hydrogel can be reduced by the addition of a reducing agent.

9. The method of claim 8, wherein the reducing agent is selected from the group consisting of dithiothreitol (DTT), 2-mercaptoethanol, dithioerythritol, cysteine, butanethiol, sodium borohydride, cyanoborohydride, mercaptoethylamine, ethylmaleimide, and tri(2-carboxyethyl)phosphine hydrochloride (TCEP.HCl).

10. The method of claim 2, wherein the solution can be oxidized by atmospheric oxygen.

11. The method of claim 1, wherein the reversible hydrogel system comprises a drug or particles.

12. The method of claim 11, wherein the particles are proteins, polymers, or inorganic compounds.

13. The method of claim 11, wherein the particles are nanoparticles.

14. The method of claim 13, wherein the nanoparticles have sizes from about 4 nanometers (nm) to about 100 nm.

15. The method of claim 13, wherein the nanoparticles do not scatter visible light.

* * * * *